(12) United States Patent
Ozuna et al.

(10) Patent No.: US 8,474,505 B2
(45) Date of Patent: Jul. 2, 2013

(54) TEMPORARY TATTOO APPLICATORS

(75) Inventors: Melissa Ozuna, Redondo Beach, CA (US); Erika Kane, San Pedro, CA (US); Craig Stock, Torrance, CA (US)

(73) Assignee: Mattel, Inc., El Segundo, CA (US)

( * ) Notice: Subject to any disclaimer, the term of this patent is extended or adjusted under 35 U.S.C. 154(b) by 669 days.

(21) Appl. No.: 12/426,843

(22) Filed: Apr. 20, 2009

(65) Prior Publication Data

US 2009/0260567 A1 Oct. 22, 2009

Related U.S. Application Data

(60) Provisional application No. 61/125,082, filed on Apr. 21, 2008, provisional application No. 61/125,417, filed on Apr. 23, 2008.

(51) Int. Cl.
| | | |
|---|---|---|
| *B05C 11/00* | (2006.01) | |
| *B65C 11/00* | (2006.01) | |
| *B41L 27/26* | (2006.01) | |
| *B41L 13/00* | (2006.01) | |
| *B41K 1/42* | (2006.01) | |
| *B41K 1/38* | (2006.01) | |
| *B41K 1/56* | (2006.01) | |
| *B41F 19/02* | (2006.01) | |
| *B41J 1/60* | (2006.01) | |
| *A63H 3/00* | (2006.01) | |
| *A63H 33/30* | (2006.01) | |

(52) U.S. Cl.
USPC ........... 156/578; 118/600; 101/121; 101/125; 101/333; 101/327; 101/405; 101/334; 101/111; 101/18; 446/73; 446/475; 446/473

(58) Field of Classification Search
USPC ............... 118/600; 156/578; 428/195.1, 40.1; 446/296, 73, 475, 901, 472, 425, 426, 427, 446/473, 483, 489, 491, 3; 101/327, 405, 101/103, 333, 334, 328, 368, 406, 111, 18, 101/134
See application file for complete search history.

(56) References Cited

U.S. PATENT DOCUMENTS 2,335,992 A * 12/1943 Biskind .......................... 101/125
2,556,258 A * 6/1951 Denison, Jr. .................... 269/25

(Continued)

FOREIGN PATENT DOCUMENTS

JP 2007152931 6/2007
JP 2007283534 A * 11/2007

OTHER PUBLICATIONS

U.S. Receiving Office, International Preliminary Report on Patentability regarding Application No. PCT/US2009/041150, Nov. 4, 2010, 7 pages.

(Continued)

*Primary Examiner* — Philip Tucker
*Assistant Examiner* — Alex Efta
(74) *Attorney, Agent, or Firm* — Kolisch Hartwell, PC

(57) ABSTRACT

A tattoo applicator for applying temporary tattoos to a subject, the tattoo applicator including a handheld housing and a sponge moveably supported by the housing to moisten the temporary tattoo and to apply pressure to the temporary tattoo. In some examples, the housing defines a retaining slot for receiving a tattoo-forming sheet. In some examples, the tattoo applicator includes a timer. In some examples, the tattoo applicator includes a push rod and a tattoo mount supported by the housing, the tattoo mount defining a port through which the push rod extends. In some examples, the tattoo applicator includes a fluid reservoir mounted to the housing.

21 Claims, 3 Drawing Sheets

U.S. PATENT DOCUMENTS

| | | | | |
|---|---|---|---|---|
| 3,214,862 A | | 11/1965 | Price | |
| 3,327,623 A | * | 6/1967 | Diegel | 101/18 |
| 3,331,315 A | * | 7/1967 | Walton | 101/68 |
| 3,521,555 A | * | 7/1970 | Price et al. | 101/103 |
| 3,898,357 A | | 8/1975 | Miller | |
| 4,004,503 A | | 1/1977 | Dwyer | |
| 4,006,786 A | * | 2/1977 | Speicher | 173/15 |
| 4,048,918 A | * | 9/1977 | Peck | 101/114 |
| 4,183,328 A | | 1/1980 | Lawrence | |
| 4,187,772 A | | 2/1980 | Hollenbeck | |
| 4,522,864 A | | 6/1985 | Humason | |
| 4,593,618 A | | 6/1986 | Lebensfeld | |
| 4,594,276 A | | 6/1986 | Relyea | |
| 4,924,773 A | | 5/1990 | Gwilliam | |
| 5,049,107 A | | 9/1991 | De Nittis | |
| 5,178,067 A | | 1/1993 | Collier | |
| 5,205,214 A | * | 4/1993 | Seo et al. | 101/333 |
| 5,253,581 A | * | 10/1993 | Miki et al. | 101/121 |
| 5,410,962 A | | 5/1995 | Collier | |
| 5,421,765 A | | 6/1995 | Lehmann et al. | |
| 5,431,098 A | | 7/1995 | Winston | |
| 5,578,353 A | | 11/1996 | Drew | |
| 5,579,692 A | | 12/1996 | Collier | |
| 5,601,859 A | | 2/1997 | Penaluna | |
| 5,727,946 A | | 3/1998 | Rosen | |
| 5,738,011 A | | 4/1998 | Tay | |
| 5,743,185 A | | 4/1998 | Hippely et al. | |
| 5,832,832 A | | 11/1998 | Carsel | |
| 5,857,411 A | | 1/1999 | Carsel | |
| 5,908,000 A | | 6/1999 | Spychalla | |
| 5,913,315 A | | 6/1999 | Todd | |
| 5,928,797 A | | 7/1999 | Vineberg | |
| 5,992,319 A | | 11/1999 | Hsu | |
| 6,032,580 A | | 3/2000 | Lee | |
| 6,139,394 A | | 10/2000 | Maxim | |
| 6,253,673 B1 | | 7/2001 | Chen | |
| 6,264,786 B1 | | 7/2001 | Cromett | |
| 6,309,088 B1 | | 10/2001 | Chen | |
| 6,315,480 B1 | | 11/2001 | Martel | |
| 6,341,882 B1 | | 1/2002 | Lin | |
| 6,499,398 B2 | * | 12/2002 | MacNeil | 101/327 |
| 6,558,221 B1 | | 5/2003 | Yang | |
| 6,588,301 B1 | * | 7/2003 | Chanet et al. | 81/9.22 |
| 6,857,935 B1 | | 2/2005 | Dohan | |
| 7,329,035 B2 | | 2/2008 | Feliciano | |
| 8,006,615 B1 | * | 8/2011 | Allen et al. | 101/125 |
| 2005/0011378 A1 | | 1/2005 | Shuler | |
| 2006/0154031 A1 | | 7/2006 | Tomlinson | |
| 2006/0233596 A1 | | 10/2006 | Fisher | |
| 2007/0292344 A1 | | 12/2007 | Turner | |

OTHER PUBLICATIONS

International Search Report and Written Opinion for related Application No. PCTUS2009041150, dated Jun. 8, 2009.

Intellectual Property Office, Examination Report Under Section 18(3) for UK Application No. GB1019449.6, Jan. 3, 2012, 2 pages.

* cited by examiner

TEMPORARY TATTOO APPLICATORS

RELATED APPLICATIONS

The present application claims the benefit of U.S. Provisional Patent Application Ser. No. 61/125,082 filed on Apr. 21, 2008, and U.S. Provisional Patent Application Ser. No. 61/125,417 filed on Apr. 23, 2008. The complete disclosures of all of the above applications are hereby incorporated by reference herein in their entirety and for all purposes.

BACKGROUND

Temporary tattoo applicators are used to non-permanently decorate skin, hair, clothing, toys or other subjects. Subjects are decorated with temporary tattoos by transferring an image from the temporary tattoo to the subject of interest. Applying temporary tattoos is known to be a source of entertainment, amusement, and artistic expression.

Traditional tattoos are images made by applying permanent pigments under the skin, or by raising scars on the skin. Thus, traditional tattoos are essentially permanent, being removable, if at all, only through complicated medical procedures. In view of this technical definition of the word "tattoo," the use of the word in the present disclosure is somewhat of a misnomer because the disclosed applicators are directed to applying non-permanent images. It is believed, however, that it has become accepted in the trade to refer to various skin decorations as tattoos, even if they are not permanent. Throughout the disclosure, temporary tattoos or decals will generally be used, but the use of tattoos alone may also be used with the understanding that the present disclosure is directed to non-permanent tattoos.

Tattoos and other skin decorations long have fascinated both children and adults, but often are avoided because of the permanence of the resulting image. Accordingly, temporary tattoos have been developed, including those applied as an ink transfer, a stamp, and a decal. Further, computer printable temporary tattoos are known in the art.

Examples of temporary tattoos and temporary tattoo applicators include U.S. Pat. No. 3,214,862, U.S. Pat. No. 3,898,357, U.S. Pat. No. 4,183,328, U.S. Pat. No. 4,187,772, U.S. Pat. No. 4,522,864, U.S. Pat. No. 4,593,618, U.S. Pat. No. 4,924,773, U.S. Pat. No. 5,049,107, U.S. Pat. No. 5,178,067, U.S. Pat. No. 5,410,962, U.S. Pat. No. 5,421,765, U.S. Pat. No. 5,431,098, U.S. Pat. No. 5,578,353, U.S. Pat. No. 5,579,692, U.S. Pat. No. 5,601,859, U.S. Pat. No. 5,727,946, U.S. Pat. No. 5,738,011, U.S. Pat. No. 5,743,185, U.S. Pat. No. 5,832,832, U.S. Pat. No. 5,857,411, U.S. Pat. No. 5,928,797, U.S. Pat. No. 5,992,319, U.S. Pat. No. 6,032,580, U.S. Pat. No. 6,139,394, U.S. Pat. No. 6,253,673, U.S. Pat. No. 6,264,786, U.S. Pat. No. 6,309,088, U.S. Pat. No. 6,341,882, U.S. Pat. No. 6,558,221 and U.S. Pat. No. 732,903; U.S. Patent Publication Nos. US20050011378 and US20070292344; and Japanese Patent No. JP2007152931. The complete disclosures of the above patents and patent applications are herein incorporated by reference for all purposes.

SUMMARY

A tattoo applicator for applying temporary tattoos to a subject, the tattoo applicator including a handheld housing and a sponge moveably supported by the housing to moisten the temporary tattoo and to apply pressure to the temporary tattoo. In some examples, the housing defines a retaining slot for receiving a tattoo-forming sheet. In some examples, the tattoo applicator includes a timer. In some examples, the tattoo applicator includes a push rod and a tattoo mount supported by the housing, the tattoo mount defining a port through which the push rod extends. In some examples, the tattoo applicator includes a fluid reservoir mounted to the housing.

DETAILED DESCRIPTION

Temporary tattoo applicators as disclosed herein will become better understood through review of the following detailed description in conjunction with the drawings and the claims. The detailed description, drawings, and claims provide merely examples of the various inventions described herein. Those skilled in the art will understand that the disclosed examples may be varied, modified, and altered without departing from the scope of the inventions as defined in the claims, and all equivalents to which they are entitled. Many variations are contemplated for different applications and design considerations; however, for the sake of brevity, each and every contemplated variation is not individually described in the following detailed description.

Throughout the following detailed description, a variety of examples of temporary tattoo applicators are provided. Related reference numbers (e.g., 12, 112, 212) are used for related features in each example. Related features may be identical, similar, or dissimilar in different examples. For the sake of brevity, related features are not redundantly explained in each example. Instead, the use of related numbers shall cue the reader that the feature with a related number may be similar to the related feature in an example explained previously. Features specific to a given example are described in that particular example. The reader should understand that a given feature need not be the same or similar to the specific portrayal of a related feature in any given figure or example.

Figure 1:
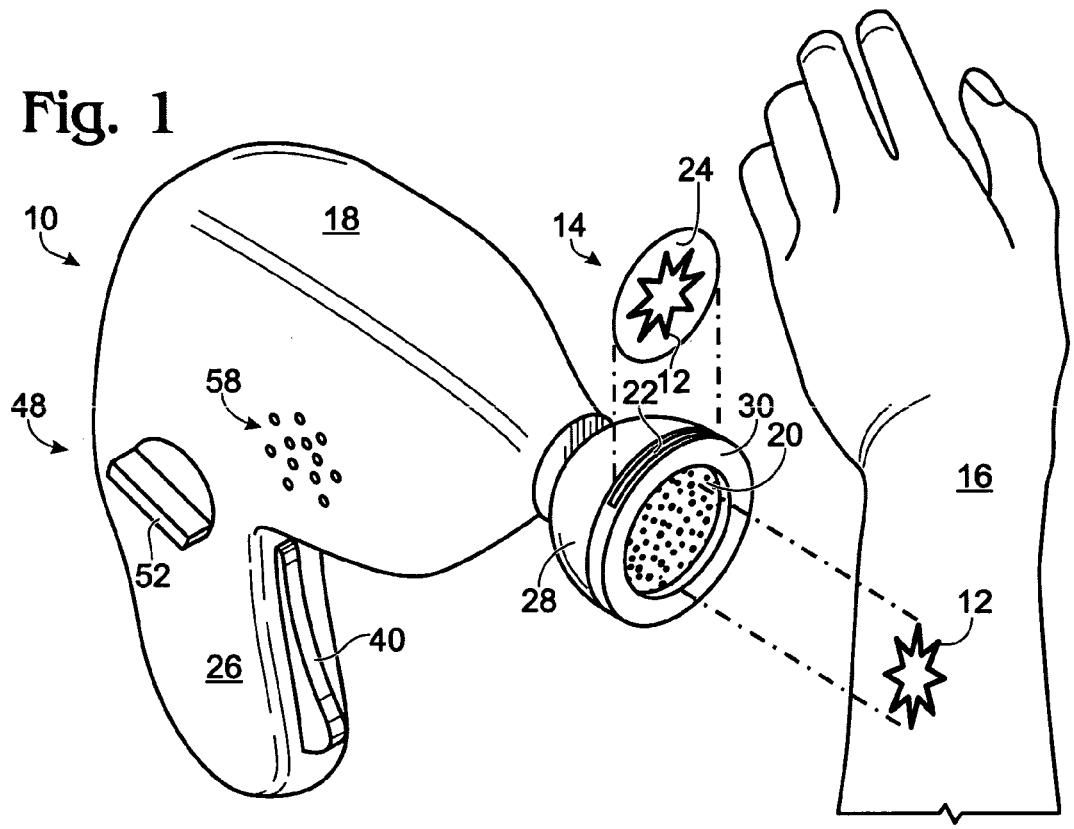
FIG. 1 is a perspective view of a tattoo applicator near a subject that has been tattooed.
Figure 3:
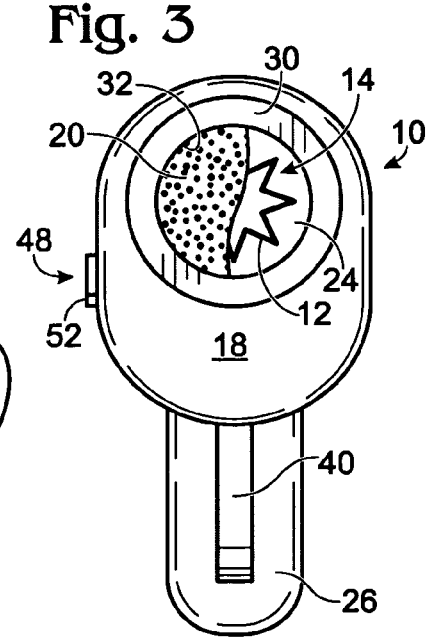
FIG. 3 is an end elevation view of the tattoo applicator of FIG. 1.
Figure 2:
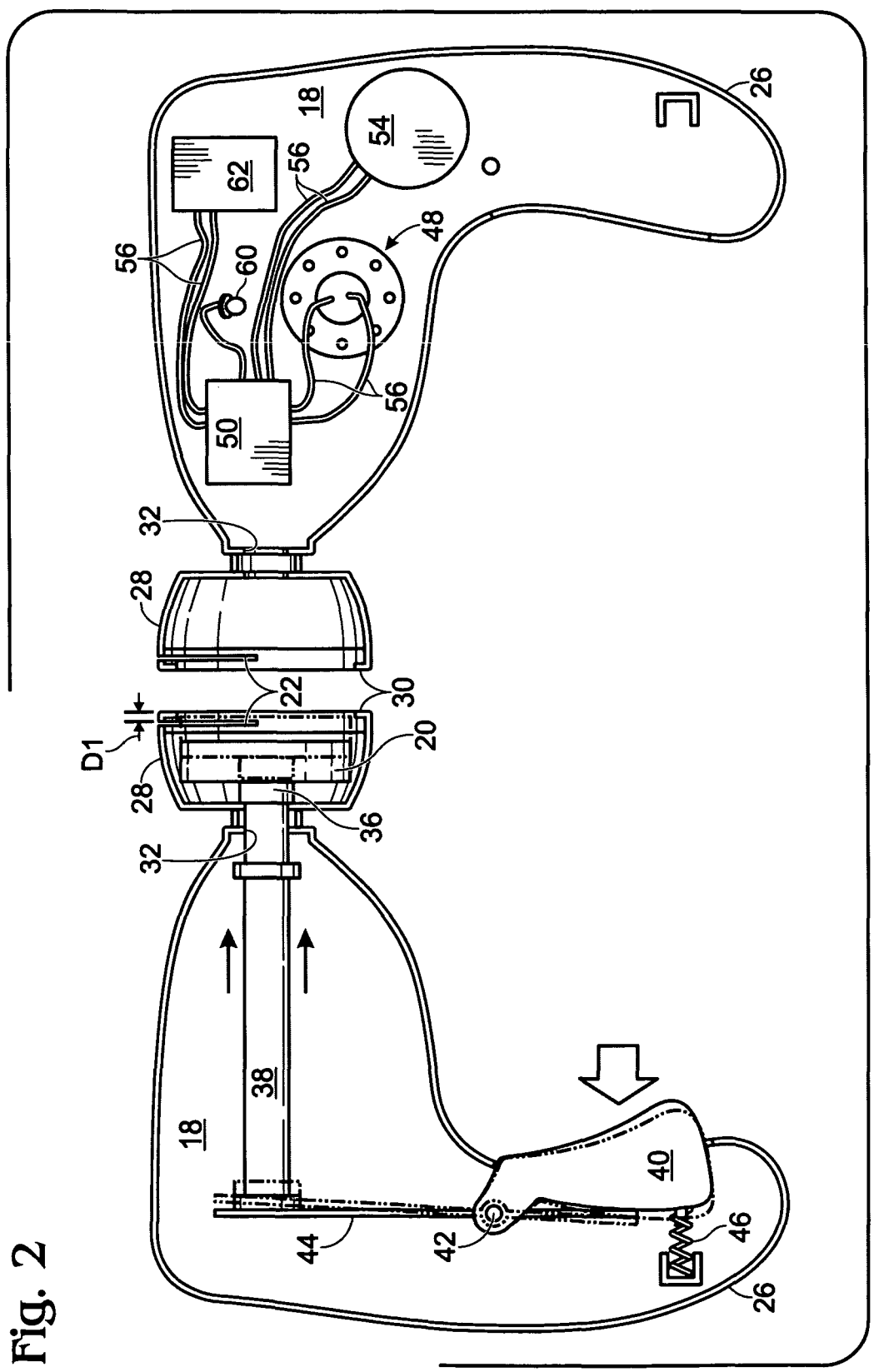
FIG. 2 is a plan view of the tattoo applicator of FIG. 1 with a handheld housing opened up into two portions to depict internal components.

With reference to FIGS. 1-3, a temporary tattoo applicator 10 for transferring an image 12 from a tattoo-forming sheet 14 onto a subject 16 will now be described. In the example shown in FIGS. 1-3, applicator 10 includes a handheld housing 18, a sponge 20, and a retaining slot 22 formed in handheld housing 18 adjacent sponge 20. As shown in FIG. 1, temporary tattoo-forming sheet 14 may be placed into retaining slot 22 to bring temporary tattoo-forming sheet near sponge 20.

Image 12 may be formed from any suitable combination of ink, pigment, and glue known in the temporary tattoo art. A supplier or user of temporary tattoo-forming sheet (or simply tattoo) 14 may create image 12. Image 12 may be any size, shape, and color combination depending on the size of temporary tattoo 14. Image 12 may include numbers, letters, symbols, pictures, characters, abstract designs, and fingerprints.

In the example shown in FIGS. 1-3, temporary tattoo 14 includes a backing 24 onto which image 12 is printed or disposed. Backing 24 is liquid permeable and when moistened separates from image 12, which adheres to subject 16 when moistened. In operation, tattoo applicator 10 enables a user to selectively cause fluid stored in sponge 20 to moisten backing 24 and image 12.

In the example shown in FIG. 1, handheld housing 18 includes a handle 26 and resembles a gun, drill or hairdryer. The form of handheld housing 18 enables a user, such as a child, to easily manipulate handheld housing 18. However, any form that accommodates the components of applicator 10 may be used. For example, the handheld housing may resemble a wand, brush, animal, vehicle or fanciful creature.

Handheld housing 18 supports a tattoo mount 28 at the end of housing 18 closest to subject 16 in FIG. 1. Tattoo mount 28 may be a separate component from housing 18 or may be integrally formed with housing 18. In the example shown in FIGS. 1-3, tattoo mount 28 defines a leading face 30 and a port 32 in which sponge 20 is mounted.

Sponge 20 stores fluid for moistening backing 24 and transferring image 12 onto subject 16. Similar to the example shown in FIGS. 4 and 5, which are discussed in more detail below, fluid may be supplied to sponge 20 from a reservoir mounted inside housing 18. Additionally or alternatively, fluid may be supplied to sponge 20 from an external source. For example, an external basin (not pictured) containing fluid may be selectively attached and detached from housing 18 to supply sponge 20 with fluid.

In the example shown in FIGS. 1-3, sponge 20 is mounted to a leading end 36 of a push rod 38. As shown in FIG. 2, push rod 38 is mounted to housing 18 on bearings that enable it to translate or slide relative to housing 18. With reference to FIG. 2, push rod 38 translates between a retracted position (shown in solid lines in FIG. 2) and an extended position (shown in dashed lines in FIG. 2).

Temporary tattoo applicator 10 may include a trigger 40 for moving push rod 38 between the retracted and extended positions when squeezed by a user. In the example shown in FIGS. 1-3, trigger 40 is pivotally mounted to housing 18 at a pivot 42. Trigger 40 is in contact with a link 44, which is also pivotally connected to pivot 42 and extends to push rod 38.

As can be seen in FIG. 2, a user pivoting trigger 40 drives link 44 to move push rod 38 between the retracted and extended positions. A biasing member 46 is provided to bias push rod 38 into the retracted position by acting on trigger 40.

As shown in FIGS. 1 and 2, a retaining slot 22 for receiving temporary tattoo 14 is defined in tattoo mount 28. In the example shown in FIGS. 1-3, retaining slot 22 is formed in tattoo mount 28 in a position where temporary tattoo 14 is disposed across port 40 and adjacent sponge 20 when inserted into retaining slot 22.

In the example shown in FIGS. 1-3, retaining slot 22 is located in a position spaced from sponge 20 when sponge 20 is in the retracted position. Temporary tattoo 14 being spaced from sponge 20 allows the user to selectively moisten temporary tattoo 14 by moving push rod 38, and thus sponge 20, to the extended position. In some examples, the retaining slot is defined in a position such that temporary tattoo 14 is in contact with sponge 20 when inserted into the retaining slot.

With reference to FIG. 2, sponge 20 extends past retaining slot 22 when push rod 38 is in the extended position. Sponge 20 extending past retaining slot 22 enables sponge 20 to apply pressure to temporary tattoo 14 when push rod 38 is in the extended position. Applying pressure to temporary tattoo 14, such as for approximately 30 seconds, helps facilitate transfer of image 12 to subject 16.

Retaining slot 22 is located at an extreme forward end of tattoo mount 38. As shown in FIG. 2, the position of retaining slot 22 limits the space or distance D1 between temporary tattoo 14 retained within retaining slot 22 and subject 16 when tattoo applicator 10 is positioned adjacent subject 16 to transfer image 12. A relatively small distance D1 between temporary tattoo 14 and subject 16 helps ensure that temporary tattoo 14 can be placed in contact with subject 16 to more effectively transfer image 12 to subject 16.

In the example shown in FIGS. 1-3, retaining slot 22 extends to the sides of housing 18 to enable a user to position temporary tattoo 14 into a desired orientation. Retaining slot 22 extending to the sides of housing 18 provides access to the periphery of temporary tattoo 14 when it is inserted into retaining slot 22. With this access, a user may rotate and slide temporary tattoo 14 into and out of retaining slot 22.

In the example shown in FIGS. 1-3, tattoo applicator 10 includes a timer 48 electrically coupled to a microprocessor 50. Timer 48 determines when a preset span of time or a user specified span of time has elapsed. While timer 48 is configured to interface with microprocessor 50 to perform its timing functions, any type of timer known in the art, such as mechanical timers, may be used with or without microprocessors.

In the example shown in FIGS. 1-3, timer 48 includes a knob or dial 52, which is accessible from outside handheld housing 18 and is configured to be rotated to a given position corresponding to a selected span of time by a user. Additionally or alternatively, timer 48 may include digital input means, such as buttons or a touch screen, or may include a mechanical slider mechanism to enable a user to input a desired span of time.

In some examples, such as the one shown in FIGS. 1-3, tattoo applicator 10 includes a sound producing device 54 to entertain and/or signal an event to a user. With reference to FIG. 2, sound producing device 54 is mounted inside handheld housing 18 and electrically connected to a microprocessor 50 with wires 56. Sound producing device 54 may be any device known in the art for producing sounds and may include any manner of speaker and sound processing circuitry.

In the example shown in FIGS. 1-3, sound producing device 54 produces a sound to indicate that a selected span of time has elapsed when receiving a signal from microprocessor 50. In this manner, the user is informed when it becomes unnecessary to apply further pressure to temporary tattoo 14 via sponge 20. Additionally or alternatively, the sound device producing device may be directly connected to timer 48.

Sound producing device 54 may produce any manner of sounds. In some examples, sound producing device 54 produces songs, spoken instructions, tones, or sound effects, such as a chime, a bell ringing, or fireworks sound effects. As shown in FIG. 1, handheld housing 18 defines holes 58 located adjacent sound producing device 54 to facilitate the produced sounds being clearly audible outside of housing 18.

In the example shown in FIGS. 1-3, tattoo applicator 10 includes a light producing device 60 to entertain and/or signal an event to a user, such as when it is unnecessary to apply further pressure to temporary tattoo 14. Light producing device 60 is electrically connected to microprocessor 50 via wires 60 for receiving signals to produce light and to stop producing light. Light producing device 60 may be any type of lighting device known in the art, such as an LED, a filament light bulb, or a florescent light. A battery 62 electrically coupled to microprocessor 50 is provided to power any components that require a power source, such a microprocessor 50, sound producing device 54, and/or light producing device 60.

Figure 4:
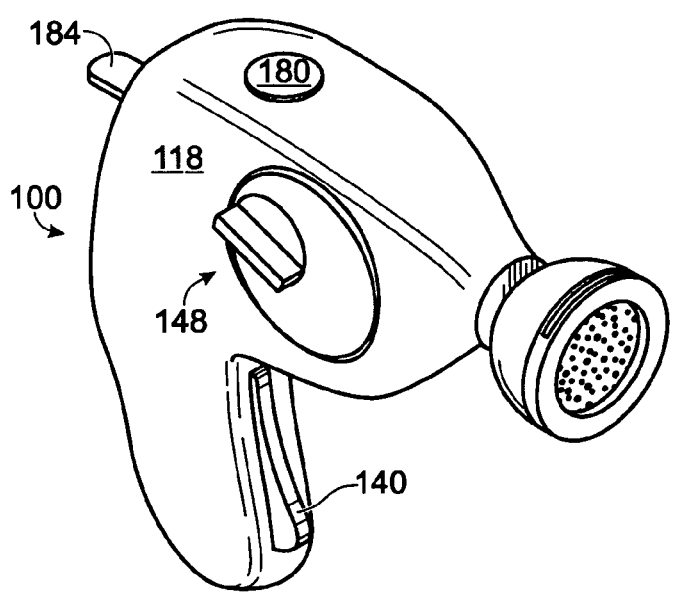
FIG. 4 is a perspective view of a tattoo applicator that includes a fluid reservoir.
Figure 5:
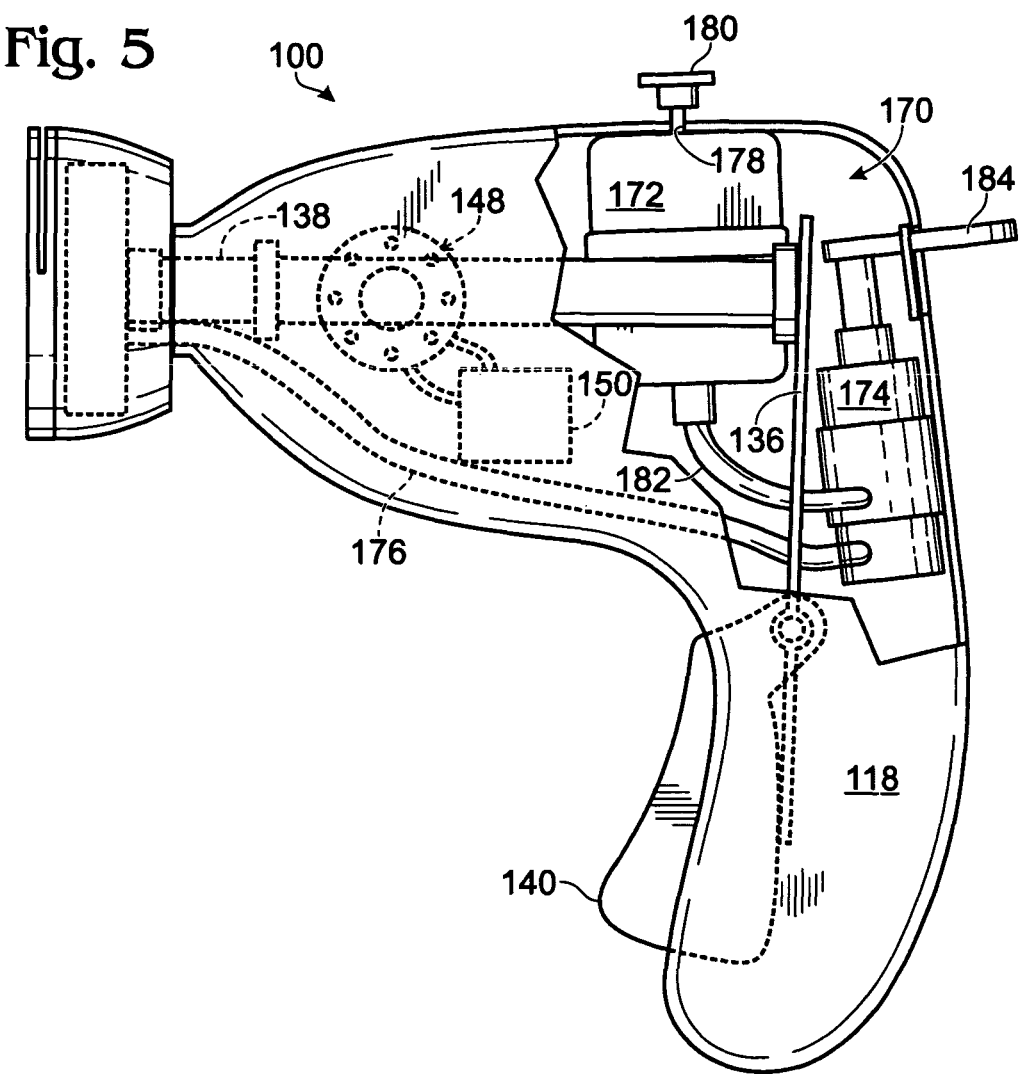
FIG. 5 is a plan view of the tattoo applicator of FIG. 4 with a portion of a handheld housing removed to show internal components.

Turning attention to FIGS. 4 and 5, a temporary tattoo applicator 100 is shown and now described. Temporary tattoo applicator 100 is similar to temporary tattoo applicator 10 except that it includes an onboard fluid source 170. Onboard fluid source 170 is described below, but first the common features and operating characteristics between tattoo applicators 10 and 100 are briefly described.

With reference to FIGS. 4 and 5, applicator 100 includes a handheld housing 118 supporting a trigger 140, that pivots a link 136 when pulled. Link 136 slides a push rod 138 forward when pivoted, which extends and retracts a sponge 120. A timer 148, which is electrically coupled to a microprocessor 150, is mounted to handheld housing for indicating when a given span of time has elapsed.

Onboard fluid source 170 shown in FIG. 5 serves to selectively moisten sponge 120. Onboard fluid source 170 includes a reservoir 172 for storing a fluid and a pump 174 for moving the fluid through a discharge conduit 176. As shown in FIG. 5, discharge conduit 176 extends from pump 174 to sponge 120.

Reservoir 172 defines a volume for storing a liquid, such as water. Reservoir 172 includes a fill port 178 for adding more fluid to reservoir 172. A cap 180 is provided to selectively cover and open fill port 178. An inlet conduit 182 fluidly connects reservoir 172 and pump 174.

As shown in FIGS. 4 and 5, pump 174 includes an actuator 184 for driving fluid through discharge conduit 176. Actuator 184 is accessible outside of handheld housing 118 and mounted to slide up and down in the orientation shown in FIG. 5. A user pushing actuator 184 downward drives fluid out of pump 174 toward sponge 120 through discharge conduit 176. Sponge 120 absorbs the fluid from discharge conduit 176 and thereby becomes selectively moistened.

It is believed that the disclosure set forth above encompasses multiple distinct inventions with independent utility. While each of these inventions has been disclosed in a particular form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Where the disclosure or subsequently filed claims recite "a" or "a first" element or the equivalent thereof, it is within the scope of the present inventions that such disclosure or claims may be understood to include incorporation of one or more such elements, neither requiring nor excluding two or more such elements.

Applicant reserves the right to submit claims directed to certain combinations and subcombinations that are directed to one or more of the disclosed inventions and that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to a different invention or directed to the same invention, whether different, broader, narrower or equal in scope to the original claims, are also regarded as included within the subject matter of the inventions of the present disclosure.

What is claimed is:

1. A tattoo applicator, comprising:
    a handheld housing having a first end with a handle and a second end with an opening;
    a sponge supported by the handheld housing and disposed between the handle and the opening;
    a retaining slot formed in the handheld housing and disposed between the sponge and the opening, the retaining slot being configured to retain a tattoo-forming sheet parallel to the sponge and the opening, the retaining slot being accessible from external the handheld housing other than through the opening so that the tattoo-forming sheet may be placed in the retaining slot by aligning the tattoo-forming sheet adjacent to the retaining slot and in a plane parallel to the sponge and inserting, from external the handheld housing, the tattoo-forming sheet into the retaining slot while in the plane; and
    a timer supported by the housing and configured to indicate when a selected span of time has elapsed, the timer including a user accessible dial configured to be rotated to a given position corresponding to the selected span of time.

2. The tattoo applicator of claim 1, wherein the sponge is mounted to a push rod slidingly mounted within the handheld housing and configured to slide in response to user input.

3. The tattoo applicator of claim 1, wherein the retaining slot is spaced only a small distance from a subject onto which a tattoo is applied when the tattoo applicator is positioned adjacent the subject to apply the tattoo.

4. The tattoo applicator of claim 1, further comprising a fluid reservoir mounted within the handheld housing and fluidly connected to the sponge.

5. The tattoo applicator of claim 4, further comprising a pump operatively connected to the fluid reservoir to selectively move fluid from the fluid reservoir to the sponge.

6. A tattoo applicator, comprising:
    a housing;
    a sponge moveably supported by the housing;
    a tattoo mount supported by the housing and configured to support a tattoo, wherein the sponge is configured to move between a retracted position in which the sponge is spaced from the tattoo, and an extended position in which the sponge contacts and presses the tattoo onto a subject to be tattooed;
    a trigger operatively connected to the sponge so that activating the trigger causes the sponge to move between the retracted and extended positions; and
    a timer supported by the housing and configured to indicate when a selected span of time has elapsed, the timer including a user accessible dial configured to be rotated to a given position corresponding to the selected span of time.

7. The tattoo applicator of claim 6, wherein the housing defines a handle for a user to hold.

8. A tattoo applicator, comprising:
    a housing;
    a tattoo mount defining a leading face and configured to support a tattoo, the tattoo mount being supported by the housing and defining a port extending through the tattoo mount to the leading face;
    a push rod movingly supported by the housing and extending into the port;
    a sponge mounted onto a leading end of the push rod, the push rod being configured to move between a retracted position in which the sponge is spaced from the tattoo, and an extended position in which the sponge contacts and presses the tattoo onto a subject to be tattooed;
    a trigger operatively connected to the push rod so that activating the trigger causes the push rod to move between the retracted and extended positions; and
    a timer supported by the housing and configured to indicate when a selected span of time has elapsed, the timer including a user accessible dial configured to be rotated to a given position corresponding to the selected span of time.

9. The tattoo applicator of claim 8, wherein the push rod is configured to move through the port, the sponge being recessed relative to the leading face when the push rod is in the retracted position, and extending toward the leading face when the push rod is in the extended position.

10. The tattoo applicator of claim 9, further comprising a biasing member that biases the push rod to the retracted position.

11. The tattoo applicator of claim 8, wherein the tattoo mount defines a slot adjacent the leading face to retain a tattoo in a position across the port.

12. A tattoo applicator, comprising:
a handheld housing;
a tattoo-forming sheet supported by the handheld housing in a position facing a subject to be tattooed, the tattoo-forming sheet including a backing and at least one tattoo disposed on the backing, the backing being configured to separate from the at least one tattoo when the backing is moistened, the at least one tattoo being configured to adhere to a subject to be tattooed when moistened; and
a sponge moveably mounted to the handheld housing and configured to moisten the backing and the at least one tattoo, to separate the at least one tattoo from the backing, and to press the moistened at least one tattoo onto the subject to be tattooed to allow the moistened at least one tattoo to adhere to the subject; and
a timer supported by the housing and configured to indicate when a selected span of time has elapsed, the timer including a user accessible dial configured to be rotated to a given position corresponding to the selected span of time.

13. The tattoo applicator of claim 12, further comprising a trigger operatively connected to the sponge so that pulling the trigger causes the sponge to move.

14. The tattoo applicator of claim 12, further comprising a fluid reservoir mounted within the housing and fluidly connected to the sponge.

15. The tattoo applicator of claim 14, further comprising a pump operatively connected to the fluid reservoir to selectively move fluid from the fluid reservoir to the sponge.

16. The tattoo applicator of claim 12, wherein:
the handheld housing includes a push rod and a trigger, the push rod being configured to translate in response to movement of the trigger; and
the sponge is mounted to the push rod.

17. A tattoo applicator, comprising:
a housing;
a sponge moveably supported by the housing;
a tattoo mount supported by the housing and configured to support a tattoo, wherein the sponge is configured to move between a retracted position in which the sponge is spaced from the tattoo, and an extended position in which the sponge contacts and presses the tattoo onto a subject to be tattooed;
a trigger operatively connected to the sponge so that activating the trigger causes the sponge to move between the retracted and extended positions;
a timer supported by the housing and configured to indicate when a selected span of time has elapsed, the timer including a user accessible dial configured to be rotated to a given position corresponding to the selected span of time; and
a sound producing device operatively connected to the timer, the sound producing device being configured to produce a sound when a user selected span of time has elapsed.

18. A tattoo applicator, comprising:
a housing;
a sponge moveably supported by the housing;
a tattoo mount supported by the housing and configured to support a tattoo, wherein the sponge is configured to move between a retracted position in which the sponge is spaced from the tattoo, and an extended position in which the sponge contacts and presses the tattoo onto a subject to be tattooed;
a trigger operatively connected to the sponge so that activating the trigger causes the sponge to move between the retracted and extended positions;
a timer supported by the housing and configured to indicate when a selected span of time has elapsed, the timer including a user accessible dial configured to be rotated to a given position corresponding to the selected span of time; and
a light producing device operatively connected to the timer, the light producing device being configured to produce light when a user selected span of time has elapsed.

19. A tattoo applicator, comprising:
a housing;
a timer supported by the housing and configured to indicate when a selected span of time has elapsed;
a sponge supported by the housing;
a tattoo mount supported by the housing in a position where a tattoo mounted on the tattoo mount is adjacent the sponge; and
at least one of:
a user accessible dial configured to be rotated to a given position corresponding to the selected span of time;
a sound producing device operatively connected to the timer, the sound producing device being configured to produce a sound when a user selected span of time has elapsed, and
a light producing device operatively connected to the timer, the light producing device being configured to produce light when a user selected span of time has elapsed.

20. A tattoo applicator, comprising:
a housing;
a sponge moveably supported by the housing;
a tattoo mount supported by the housing and configured to support a tattoo, wherein the sponge is configured to move between a retracted position in which the sponge is spaced from the tattoo, and an extended position in which the sponge contacts and presses the tattoo onto a subject to be tattooed;
a trigger operatively connected to the sponge so that activating the trigger causes the sponge to move between the retracted and extended positions;
a timer supported by the housing and configured to indicate when a selected span of time has elapsed; and
a sound producing device operatively connected to the timer, the sound producing device being configured to produce a sound when a user selected span of time has elapsed.

21. A tattoo applicator, comprising:
a housing;
a sponge moveably supported by the housing;
a tattoo mount supported by the housing and configured to support a tattoo, wherein the sponge is configured to move between a retracted position in which the sponge is spaced from the tattoo, and an extended position in which the sponge contacts and presses the tattoo onto a subject to be tattooed;

a trigger operatively connected to the sponge so that activating the trigger causes the sponge to move between the retracted and extended positions;
a timer supported by the housing and configured to indicate when a selected span of time has elapsed; and
a light producing device operatively connected to the timer, the light producing device being configured to produce light when a user selected span of time has elapsed.

\* \* \* \* \*